United States Patent
Wang et al.

(10) Patent No.: US 7,642,095 B2
(45) Date of Patent: Jan. 5, 2010

(54) METHOD OF ANALYZING BASESTOCKS FOR LOW TEMPERATURE PROPERTIES

(75) Inventors: Frank Cheng-Yu Wang, Annandale, NJ (US); Lei Zhang, Vienna, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 169 days.

(21) Appl. No.: 11/667,234

(22) PCT Filed: Nov. 14, 2005

(86) PCT No.: PCT/US2005/041206

§ 371 (c)(1),
(2), (4) Date: Sep. 25, 2007

(87) PCT Pub. No.: WO2006/055499

PCT Pub. Date: May 26, 2006

(65) Prior Publication Data

US 2008/0206878 A1 Aug. 28, 2008

(51) Int. Cl.
*G01N 30/06* (2006.01)
*G01N 30/46* (2006.01)

(52) U.S. Cl. .............. 436/60; 436/33; 436/40; 208/18; 208/20; 208/24; 208/33

(58) Field of Classification Search .......... 436/60
See application file for complete search history.

(56) References Cited

U.S. PATENT DOCUMENTS

| 5,460,739 | A | 10/1995 | Rhodes et al. |
| 5,699,269 | A | 12/1997 | Ashe et al. |
| 2005/0077208 | A1* | 4/2005 | Miller et al. ............ 208/18 |
| 2005/0133407 | A1* | 6/2005 | Abernathy et al. ........ 208/18 |

FOREIGN PATENT DOCUMENTS

WO   WO 2005/054843 A   6/2005

OTHER PUBLICATIONS

Vendeuvre, C. et al—"Comparison of conventional gas chromatography and comprehensive two-dimensional gas chromatography for the detailed analysis of petrochemical samples", Journal of Chromatography, Elsevier Science Publishers B.V. Amsterdam, NL, vol. 1056, No. 1-2, (Nov. 12, 2004), pp. 155-162, XP004627942 ISSN: 0021-9673, abstract p. 155, col. 2, line 4—p. 156, line 26 Figure 3.

(Continued)

*Primary Examiner*—Krishnan S Menon
*Assistant Examiner*—Rebecca Fritchman
(74) *Attorney, Agent, or Firm*—Robert A. Migliorini; Gerard J. Hughes

(57) ABSTRACT

A process for producing lube basestocks involving solvent dewaxing a waxy feed to produce at least a partially dewaxed lube oil boiling range stream and then hydrodewaxing the partially dewaxed lube oil boiling range stream to produce a lube basestock.

21 Claims, 3 Drawing Sheets

OTHER PUBLICATIONS

Schoenmakers, P.J. et al—"Comparison of comprehensive two-dimensional gas chromatography and gas chromatography—mass spectrometry for the characterization of complex hydrocarbon mixtures", Journal of Chromatography, Elsevier Science Publishers B.V. Amsterdam, NL, vol. 892, No. 1-2, (Sep. 15, 2000), pp. 29-46, XP004212053, ISSN: 0021-9673, abstract p. 30, col. 1, lines 12-23, p. 31, col. 1, lines 7-17 Figures 1, 2, 7.

Kane, M. et al—"Rheology and structure of waxy crude oils in quiescent and under shearing conditions", Fuel, IPC Science and Technology Press, Guildford, GB, vol. 83, No. 11-12, (Aug. 2004) pp. 1591-1605, XP004508644, ISSN: 0016-2361 abstract.

Vendeuvre, C. et al.—"Characterisation of middle-distillates by comprehensive two-dimensional gas chromatography (GCxGC): A powerful alternative for performing various standard analysis of middle-distillates", Journal of Chromatography A, Elsevier, Amsterdam, NL, vol. 1086, No. 1-2, (Sep. 9, 2005), pp. 21-28, XP004995136, ISSN: 0021-9673 abstract p. 21, col. 2, para. 2—p. 22, col. 1, para. 1—p. 22, col. 2, para. 3, p. 25, col. 1, para. 2—p. 27, col. 2, para. 2, Figures 1, 4-7.

* cited by examiner

METHOD OF ANALYZING BASESTOCKS FOR LOW TEMPERATURE PROPERTIES

FIELD OF THE INVENTION

This invention relates to a method for analyzing a lubricating oil. The method utilizes 2-dimensional gas chromatography (2D GC) to determine the amounts of paraffins and iso-paraffins in the oil. The compositional information thus obtained is used to calculate a Paraffin Index and the Paraffin Index correlated with formulated oil Mini Rotary Viscometer (MRV).

BACKGROUND OF THE INVENTION

Modern industry standards are placing increasing demands on the low temperature performance of engine oils. The low temperature performance of formulated engine oils can be improved by improving the base oil, by improving the additives used in formulating the oil or both. The low temperature properties of base oils may also be improved by using a synthetic base oil such as a poly-alpha olefin (PAO).

The low temperature properties of any oil are influenced by the presence of waxes such as long chain paraffins. These materials are thought to form wax crystals at low temperatures. These wax materials in turn adversely affect the fluidity of the oil thus causing a deterioration of low temperature properties. It is common practice to at least partially remove waxy materials from basestocks by dewaxing. Dewaxing can be accomplished by either solvent or catalytic means. Solvent dewaxing is a physical method in which waxy molecules are separated based on their solubility properties in select solvents. Catalytic dewaxing chemically converts the waxy molecules to other molecules that have better low temperature properties. Catalytic dewaxing may occur by cracking waxy molecules or by isomerizing waxy molecules.

Another approach typically used in conjunction with dewaxing is the addition of additives such as pour point depressants as part of an additive package added to the lubricating oil basestock to form a formulated oil. Pour point depressants are generally polymeric materials that improve the fluidity of an oil, i.e., they reduce the pour point. However, any given pour point depressant will have a different influence on the pour point depending on the nature of the oil in question. While a given pour point depressant may be effective in one oil, it may be ineffective in another. Thus, it is necessary to test the low temperature properties of an oil to know the influence of any given additive package containing a pour point depressant.

One method for determining low temperature pumpability of an engine oil is based on the Mini Rotary Viscometer (MRV). Other means of measuring the low temperature properties of a formulated oil include Brookfield Viscosity, Scanning Brookfield Viscosity, Cold Cranking Simulator test (CCS) and Pour Point. While these test methods may yield information about the low temperature properties of any give oil, they do not necessarily provide information as to the compositional features of that oil.

Various physical techniques have been developed to investigate the composition of crude oils and fractions thereof, including Fourier Transform infrared spectroscopy (FTIR), liquid chromatography, gas chromatography (GC), nuclear magnetic resonance (NMR), and mass spectrometry (MS). Due to the complexity of petroleum mixtures such as crudes, no technique is capable of providing precise compositional details of all the individual molecules making up the petroleum mixture.

GC/MS methods use GC to at least partially separate a mixture into components thereof and MS is then used to identify the components. Petroleum mixtures are very difficult to resolve into individual components due to the complexity of the mixtures and the similar retention times of many individual molecules under given GC conditions.

Two-dimensional gas chromatography (2D GC) is a recent technique that has been developed as a high resolution alternative to conventional GC/MS techniques. In 2D GC, a sample is subjected to two sequential chromatographic separations. The first separation is a partial separation by a first or primary separation column. The partially separated components are then injected into a second or secondary column where they undergo further separation. The two columns usually have different selectivities to achieve the desired degree of separation. An example of 2D GC may be found in U.S. Pat. No. 5,169,039.

It would be desirable if the chromatographic separation information on molecular composition available from 2D GC could be correlated with low temperature viscometric properties of formulated oils.

SUMMARY OF THE INVENTION

This invention relates to a process for predicting the Mini Rotary Viscometer (MRV) properties of a wide range of formulated oils, preferably for use in passenger car internal combustion engines which comprises:
(a) injecting a basestock sample into a first column of a 2-dimensional gas chromatograph, said first column being coated with a non-polar material to separate the basestock sample into a series of first dimension sample components having a first set of retention times;
(b) injecting the separated first dimension sample components from step (a) into a second column coated with a semi-polar material to further separate the separated first dimension sample components into second dimension sample components having a second set of retention times;
(c) subjecting the first and second sets of retention times to qualitative analysis to identify n-paraffin and iso-paraffin components or groupings thereof and to quantitative analysis to identify the quantity of the n-paraffin components and iso-paraffin components or groupings thereof having carbon numbers in the lubricant basestock range;
(d) grouping iso-paraffin components into x groupings where x is a number from 0 to 3 for each identified individual lube paraffin in the carbon number range from 16 to 50;
(e) selecting a lower carbon number n and an upper carbon number m;
(f) identifying the n-paraffin and a first, second and third iso-paraffin group A, B and C for each individual carbon number over the range from n to m;
(g) calculating a Paraffin Index over a given carbon range bounded by a lower carbon number, n, and an upper carbon number, m, wherein the Paraffin Index is calculated by:

$$\text{Paraffin Index} = \sum_{L=n}^{m} \frac{(\text{n-paraffin})_L + (\text{Iso-paraffins group } A)_L}{(\text{Total paraffins})_L}$$

Where L is the carbon number of the each identified paraffins over the carbon range from n to m in the baseoil sample. (n-paraffin)$_L$ is the amount of the normal paraffin at each individual carbon number, (Iso-paraffins group A)$_L$ is the amount of iso-paraffins in a first group A at each individual carbon number, and (Total paraffins)$_L$ is the sum of n-paraffin plus iso-paraffin groups A, B and C at each individual carbon number;

(h) repeating steps (a)-(g) for a series of basestock samples;

(i) measuring the MRV for a series of formulated basestock samples;

(j) plotting measured MRV of the formulated basestock samples versus Paraffin Index of basestock samples to produce a plot having a slope (a) and an intercept (b); and (k) calculating the predicted MRV using the equation: MRV= (a)(Paraffin Index)–(b).

DETAILED DESCRIPTION OF THE INVENTION

Figure 1:
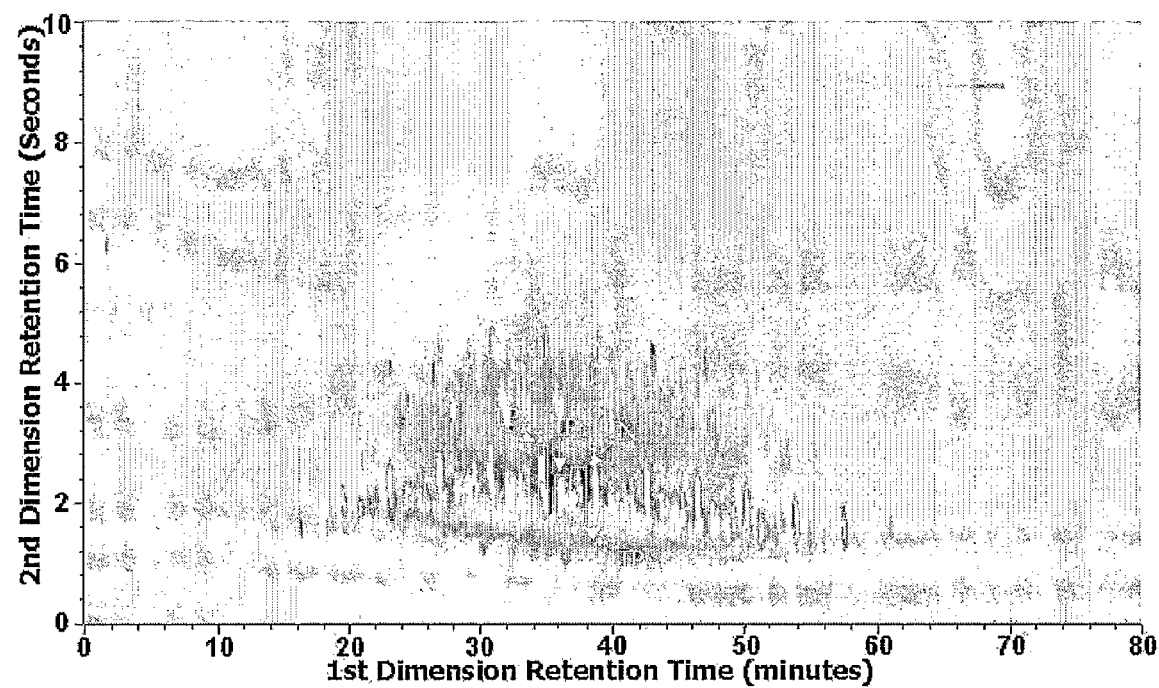
FIG. 1 is a graph showing a 2D GC of a typical 130N lube raffinate sample.

The basestocks used to formulate engine oils are typically derived from petroleum distillates having a 10% distillation point greater than 270° C. (518° F.) and a 95% distillation point less than 621° C. (1150° F.) measured by ASTM D 86 or D 2887. Because these distillates frequently contain undesirable quantities of sulfur- and/or nitrogen-containing contaminants they may be solvent extracted, hydrotreated, or both, prior to further processing. The terms "baseoil" and "basestock" are used interchangeably herein.

The solvent extraction process selectively dissolves the aromatic components in an extract phase while leaving the more paraffinic components in a raffinate phase. Naphthenes are distributed between the extract and raffinate phases. Typical solvents for solvent extraction include phenol, furfural and N-methyl pyrrolidone. By controlling the solvent to oil ratio, extraction temperature and method of contacting distillate to be extracted with solvent, one can control the degree of separation between the extract and raffinate phases. Sulfur- and nitrogen-containing contaminants are concentrated in the extract phase.

For hydrotreating, the catalysts are those effective for hydrotreating such as catalysts containing Group 6 metals (based on the IUPAC Periodic Table format having Groups from 1 to 18), Groups 8-10 metals, and mixtures thereof. Preferred metals include nickel, tungsten, molybdenum, cobalt and mixtures thereof. These metals or mixtures of metals are typically present as oxides or sulfides on refractory metal oxide supports. The mixture of metals may also be present as bulk metal catalysts wherein the amount of metal is 30 wt. % or greater, based on catalyst. Suitable metal oxide supports include oxides such as silica, alumina, silica-aluminas or titania, preferably alumina. Preferred aluminas are porous aluminas such as gamma or eta. The amount of metals, either individually or in mixtures, ranges from about 0.5 to 35 wt. %, based on the catalyst. In the case of preferred mixtures of Groups 9-10 metals with Group 6 metals, the Groups 9-10 metals are present in amounts of from 0.5 to 5 wt. %, based on catalyst and the Group 6 metals are present in amounts of from 5 to 30 wt. %. The amounts of metals may be measured by atomic absorption spectroscopy, inductively coupled plasma-atomic emission spectrometry or other methods specified by ASTM for individual metals.

The acidity of metal oxide supports can be controlled by adding promoters and/or dopants, or by controlling the nature of the metal oxide support, e.g., by controlling the amount of silica incorporated into a silica-alumina support. Examples of promoters and/or dopants include halogen, especially fluorine, phosphorus, boron, yttria, rare-earth oxides and magnesia. Promoters such as halogens generally increase the acidity of metal oxide supports while mildly basic dopants, such as yttria or magnesia, tend to decrease the acidity of such supports.

Especially preferred metal catalysts include cobalt/molybdenum (1-5 wt % Co as oxide, 10-25 wt % Mo as oxide), nickel/molybdenum (1-5 wt % Ni as oxide, 10-25 wt % Co as oxide), or nickel/tungsten (1-5 wt % Ni as oxide, 10-30% W as oxide) on alumina.

Hydrotreating conditions include temperatures of from 150° C. to 400° C., preferably 200° C. to 350° C., a hydrogen partial pressure of from 1480 to 20786 kPa (200 to 3000 psig), preferably 2859 to 13891 kPa (400 to 2000 psig), a space velocity of from 0.1 to 10 LHSV, preferably 0.1 to 5 LHSV, and a hydrogen-to-feed ratio of from 89 to 1780 m$^3$/m$^3$ (500 to 10000 scf/B), preferably 178 to 890 m$^3$/m$^3$ (1000 to 5000 scf/B).

The hydrotreated basestock may be passed directly to a dewaxing step or preferably, stripped to remove gaseous contaminants such as hydrogen sulfide and ammonia prior to dewaxing. Stripping can be by conventional means such as flash drums or fractionators.

Dewaxing

Dewaxing is one method used to control the low temperature properties of basestocks. It is generally accepted that waxy molecules such as long chain paraffins crystallize at low temperatures thereby adversely impacting cold flow properties. Thus, the removal of waxy molecules from the basestock is considered to improve the basestocks low temperature properties. Two commonly employed methods of removing waxy molecules from basestocks are solvent dewaxing, catalytic dewaxing, or a combination of solvent and catalytic dewaxing. Trim dewaxing is solvent dewaxing followed by catalytic dewaxing.

For solvent dewaxing, the dewaxing solvent used may include the $C_3$-$C_6$ ketones such as methyl ethyl ketone (MEK), methyl isobutyl ketone (MIBK), mixtures of MEK and MIBK, aromatic hydrocarbons like toluene, mixtures of ketones and aromatics like MEK/toluene, ethers such as methyl t-butyl ethers and mixtures of same with ketones or aromatics. Similarly, liquefied, normally gaseous hydrocarbons like propane, propylene, butane, butylene, and combinations thereof may be used as the solvent. Preferably, the solvent employed will be a mixture of methyl ethyl ketone and methyl isobutyl ketone.

The solvent dewaxing process typically involves mixing the lube oil boiling range feedstock with a dewaxing solvent at atmospheric pressure, separating precipitated wax and recovering solvent for recycling. The lube oil boiling range feedstock is mixed with chilled solvent to form an oil-solvent solution and precipitated wax is thereafter separated by, for example, filtration. The temperature and solvent are selected so that the oil is dissolved by the chilled solvent while the wax is precipitated.

A particularly suitable solvent dewaxing process involves the use of a cooling tower where solvent is prechilled and added incrementally at several points along the height of the cooling tower. The lube oil boiling range feedstream-solvent mixture is agitated during the chilling step to permit substantially instantaneous mixing of the prechilled solvent with the lube oil boiling range feedstream. The prechilled solvent is added incrementally along the length of the cooling tower so as to maintain an average chilling rate at or below about 10° F./minute (about –12° C./minute), usually between about 1° F. to about 5° F./minute (about –17° C. to about –15° C./minute). The final temperature of the lube oil boiling range feedstream-solvent/precipitated wax mixture in the cooling tower will usually be between 0° F. and 50° F. (–17.8° C. to 10° C.). The mixture may then be sent to a scraped surface chiller to separate precipitated wax from the mixture.

As stated above, the solvent dewaxing of the lube oil boiling range feedstream occurs under effective solvent dewaxing conditions. Effective solvent dewaxing conditions are to be considered those solvent dewaxing conditions that are capable of removing at least a portion of the wax contained in the lube oil boiling range feedstream. Generally, effective solvent dewaxing conditions will include that amount of solvent that when added to the lube oil boiling range feedstream will be sufficient to provide a liquid/solid weight ratio of about 5/1 to about 20/1 at the dewaxing temperature and a solvent/oil volume ratio between 1.5/1 to 5/1. The solvent dewaxing of the lube oil boiling range feedstream typically results in a partially dewaxed fraction having a pour point from about +30° C. to about –20° C.

Catalytic dewaxing usually involves one or both the following mechanisms: catalytic dewaxing by cracking waxy molecules or catalytic dewaxing by isomerizing waxy molecules. Catalytic dewaxing by cracking involves molecular weight reduction since waxy molecules are cracked to lower molecular weight molecules. Catalytic dewaxing by isomerization involves isomerizing waxy molecules (straight chain paraffins) to branched chain paraffins. It should be noted that very few if any dewaxing catalysts operate exclusively by one mechanism.

Catalysts for dewaxing by catalytic cracking include ZSM-5, ZSM-11, ZSM-22, ZSM-35, mordenite and beta. Since this form of dewaxing involves cracking waxy molecules, some yield loss may occur. Dewaxing catalysts may be characterized by their alpha values. The alpha value of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the *Journal of Catalysis*, 4, 522-529 (1965); 6, 278 (1966); and 61, 395 (1980), each incorporated herein by reference. Catalysts employed for dewaxing by catalytic cracking can have an alpha value greater than 100, preferably 100 to 180. The alpha value of a catalyst may be increased by initially treating the catalyst with nitric acid or by mild steaming as discussed in U.S. Pat. No. 4,326,994. Steaming is a means of adjusting the silica:alumina ratio of the catalyst and hence its alpha value.

Catalysts for dewaxing by isomerization are those which isomerize at least a portion of the waxy n-paraffin molecules to isoparaffins. Waxy molecules may be from a mineral source, synthetic source or a mixture of the two, e.g., Fischer-Tropsch wax. Such isomerization catalysts minimize the amount of dewaxing by cracking mechanisms. Because there is little molecular weight reduction associated with isomerizing catalysts, there is less yield loss as compared to dewaxing by cracking. Isomerizing dewaxing catalysts are typically metal loaded with Group 6 metals, Group 8-10 metals and mixtures thereof (based on the IUPAC format). Especially preferred metals are Groups 8-10 noble metals, especially Pt, Pd or mixtures thereof. These metals are loaded at the rate of 0.1 to 30 wt % based on catalyst.

Hydrodewaxing catalysts suitable for use herein may be either crystalline or amorphous. Amorphous hydrodewaxing catalysts include alumina, fluorided alumina, silica-alumina, and fluorided silica-alumina. Such catalysts are well known. Crystalline materials are molecular sieves that contain at least one 10- or 12-ring channel and may be based on aluminosilicates (zeolites) or on aluminophosphates such as silicoaluminophosphates (SAPOs) and magnealuminophosphates (MAPOs). Molecular sieves suitable for use herein contain at least one 10- or 12-ring channel. Examples of such zeolites include ZSM-22, ZSM-23, ZSM-35, ZSM-48, ZSM-57, ferrierite, ITQ-13, MCM-68 and MCM-71. Examples of aluminophosphates containing at least one 10-ring channel include ECR-42, SAPO-11, SAPO-31 and SAPO-41. Examples of molecular sieves containing 12-ring channels include zeolite beta and MCM-68.

The molecular sieves are typically composited with binder materials that are resistant to high temperatures and that may be employed under hydrodewaxing conditions to form a finished hydrodewaxing catalyst or may be binderless (self bound). The binder materials are usually inorganic oxides such as silica, alumina, silica-aluminas, binary combinations of silicas with other metal oxides such as titania, magnesia, thoria, zirconia and the like and tertiary combinations of these oxides such as silica-alumina-thoria and silica-alumina magnesia. The preferred binder is alumina. The amount of molecular sieve in the finished hydrodewaxing catalyst is from 10 to 100 wt. %, preferably 35 to 100 wt. %, based on catalyst. Such catalysts are formed by methods such spray drying, extrusion and the like. The hydrodewaxing catalyst may be used in the sulfided or unsulfided form, and is preferably in the sulfided form.

Effective hydrodewaxing conditions as used herein include temperatures between about 200° C. to about 400° C., preferably about 225° C. to about 350° C., more preferably 250° C. to 310° C., pressures between about 2860 to about 20786 kPa (about 400 to about 3000 psig), preferably about 4238 to about 17388 kPa (about 600 to about 2500 psig), more preferably about 4238 to about 10443 kPa (about 600 to about 1500 psig) hydrogen treat gas rates of about 89 to about 890 m$^3$/m$^3$ (about 500 to about 5,000 SCF H$_2$/B), preferably about 107 to about 445 m$^3$/m$^3$ (about 600 to about 2500 SCF H$_2$/B), and liquid hourly space velocities ("LHSV") of about 0.1 to about 10 V/V/hr, preferably about 0.1 to about 5 V/V/hr, more preferably about 0.5 to about 2 V/V/hr.

Formulated Oils

The properties of formulated oils, particularly the low temperature properties, are a function of the basestock and the additive package used to prepare the formulated oil. As noted above, the low temperature properties, e.g., the pour point, Brookfield viscosity, MRV, cold cracking simulator test (CCS) and gel index, of a basestock are adversely affected by waxes. Thus, it is advantageous to remove at least some of the waxy components of the basestock by dewaxing. The viscosity index (VI) of the oil is likewise impacted by basestock components. The VI is adversely impacted by components such as aromatics which have a low VI. The low temperature properties are also affected by whether the basestock itself is synthetic such as PAO or of mineral origin.

The MRV of a formulated base oil is an indicator of low temperature properties. The MRV is measured by standards tests such as ASTM D 3829 and D 4684. The MRV test measures the pumping performance of a formulated baseoil at low temperature. Smaller values of MRV correlate with better low temperature properties.

Another factor influencing the properties of the formulated oil is the additive package (adpak) used to formulate the oil. Additive packages contain at least one component selected from dispersants, detergents, wear inhibitors, antioxidants, rust inhibitors, demulsifiers, extreme pressure agents, friction modifiers, multifunction additives, viscosity index improvers, pour point depressants, and foam inhibitors.

Many different additive packages are commercially available. The precise formulations vary depending on the manufacturer and the intended use of the engine oil. For example, engine oils for diesel engines may contain different additive components as compared to engine oils for gasoline powered engines. Formulations for hot climates will vary from those for cold climates.

Two-Dimensional Gas Chromatography

2D GC is an alternative to gas chromatography/mass spectrometry. In 2D GC, a sample is injected into a first column and the separated components injected into a second column in series with the first.

A sample is injected into an inlet device connected to the inlet of a first column to produce a first dimension chromatogram. Sample injection may be by any known sample injection device such as a syringe. The inlet device may hold a single sample or may hold multiple samples for injection into the first column. The column contains a stationary phase that is usually the column coating material.

The first column may be coated with a non-polar material. When the column coating material is methyl silicon polymer, the polarity can be measured by the percentage of methyl group substituted by the phenyl group. The polarity of coating materials are measured on a % of phenyl group substitution scale from 0 to 100 with zero being non-polar and 80 (80% phenyl substitution) being considered as polar. These methyl silicon polymers are considered non-polar and have polarity values in the range from 0 to 20. Phenyl substituted methyl silicon polymers are considered semi-polar and have polarity values of 21 to 50. Phenyl substituted methyl silicon polymer coating materials have been called polar materials when greater than 50% phenyl substitution group is included in polymers. Other polar coating polymers, such as carbowaxes, were also used in chromatographic applications. Carbowaxes are high molecular weight polyethylene glycols. In addition, a series of carborane silicon polymers sold under the trade name Dexsil have been especially designed for high temperature applications.

The first column coated with a non-polar material provides a first separation of the sample. The first separation, also known as the first dimension, generates a series of bands over a given time period. This first dimension chromatograms is not unlike the chromatogram that could be obtained from a conventional chromatogram. The bands represent individual components or groups of components of the sample injected, and separated or partially overlapping with adjacent bands.

When the complex mixture is separated by the first dimension column, it still suffers many co-elutions that are not able to be separated by the first dimension column. The bands of separated materials from the first dimension are then sent in their entirety to the second column to perform a further separation, especially of the co-eluted components. This further separation is referred to as a second dimension. The second dimension is a second column coated with a semi-polar or polar material, preferably a semi-polar coating material.

In order to make the data acquisition as well as the detector signal meaningful, a modulator is required to manage the flow between the end of the first column and the beginning of the second column. Modulators may be thermal modulators that use a trap/release mechanism. In this mechanism, cold nitrogen gas is used to trap separated sample from the first dimension followed by a periodic pulse of hot nitrogen to release trapped sample to a second dimension. Each pulse is analogous to a sample injection into the second dimension.

The role of the modulator is (1) collect the continuous eluent flow out from the end of the first column with a fixed period of time (modulated period), and (2) inject collected eluent to the beginning of the second column by releasing collected eluent at the end of modulated period. The function of the modulator is (1) define the beginning time of a specific second dimensional column separation and (2) define the length of the second dimensional separation (modulation period).

The separated bands from the second dimension are coupled with the bands from the first dimension to form a comprehensive 2D chromatogram. The bands are placed in a retention plane wherein the first dimension retention times and the second dimension retention times form the axes of the 2D chromatogram.

For example, a conventional GC experiment takes 80 minutes to separate a mixture (a chromatogram with 80 minutes retention time, x-axis). When the same experiment is performed under 2D GC conditions with a 10-second modulation period, it will become 480 chromatograms (60 seconds× 80 minutes divided by 10 seconds) where each 10 second chromatogram (y-axis) lines up one-by-one along the retention time axis (x-axis). In 2D GC, the x-axis is the first dimension retention time (the same as conventional GC), the y-axis is the second dimensional retention time, peak intensity should stick out in the third dimension z-axis. In order to express this 3D picture on two dimensional paper, the intensity has been converted based on a pre-defined gray scale table to express their relative peak intensity by gray-scale.

FIG. 1 shows a 2D GC chromatogram of a typical 130N lube raffinate sample. In this 2D GC/FID (flame ionization detector) run, data point from the experiment dimension is 480×1000. The display dimension is: 2880×2000. Separation column set used is: 1st Column, SGE BPX-5 (BPX is a phenyl siloxane polymer), 30 meter, 0.25 mm ID, 1.0 µm Film; and 2nd Column, SGE BPX-50, 9.0 meter, 0.25 mm ID, 0.25 µm Film. Oven temperature program was set at 210° C. for 0 minutes and ramped at 1.5° C. per minute to 315° C. for 10 minutes. Flow program is 1.5 ml per minute for 0 minute and increased 0.05 ml/minute per minute to 5.0 ml per minute for 0 minute. The inlet temperature was set at 300° C. with split/splitness ratio of 75:1. The sample injection volume is 0.2 µl.

To determine the Paraffin Index, the entire paraffin components in the baseoil are identified in the carbon number range from 16 to 50. The Paraffin Index is calculated over a given carbon range bounded by a lower carbon number, n, and an upper carbon number, m, For example, the lower carbon value can be selected as n=23 and an upper carbon value as m=31 for 130N lube raffinate sample. At a given carbon number L, the normal paraffins (denoted as $N_L$). Because the resolution is not sufficient to identify individual isoparaffins, the isoparaffins are formed into groups. The isoparaffins for that carbon number are grouped into discrete groups, preferably 3 groups denoted as $(IP_A)_L$, $(IP_B)_L$, and $(IP_C)_L$. The process is repeated for each carbon number over the entire carbon number range from n to m in the 2D GC spectrum. The peak volume of each normal paraffin component and isoparaffin groups is integrated to obtain the weight percentage of a specific component to the total sample. In the 2D GC chromatogram of 130N lube raffinate, shown in FIG. 1, the calculation is performed from carbon number of 23 to 31 ($C_{23}$ to $C_{31}$). The individual component composition is summarized in the following Table 1.

TABLE 1

130N Lube Raffinate Composition Based on 2D-GC Chromatogram

| | Carbon Number | | | | | | | | |
|---|---|---|---|---|---|---|---|---|---|
| | 23 | 24 | 25 | 26 | 27 | 28 | 29 | 30 | 31 |
| N | 0.98 | 2.10 | 3.58 | 3.66 | 3.36 | 2.60 | 1.89 | 1.11 | 0.57 |
| $IP_A$ | 0.16 | 0.47 | 1.33 | 1.70 | 1.86 | 1.52 | 1.18 | 0.88 | 0.57 |
| $IP_B$ | 0.31 | 0.85 | 1.61 | 1.82 | 1.70 | 1.50 | 1.18 | 0.75 | 0.35 |
| $IP_C$ | 0.08 | 0.16 | 0.38 | 0.44 | 0.35 | 0.40 | 0.27 | 0.16 | 0.06 |

The Paraffin Index is then determined. For any given sample, the Paraffin Index is calculated over a given carbon range bounded by a lower carbon number, n, and an upper carbon number, m, by summing at each carbon number (L) the ratio of (n-paraffins plus the A group of isoparaffins) to the (n-paraffins plus the A, B and C group of isoparaffins). This is represented by the following Equation 1:

$$\text{Paraffin Index} = \sum_{L=n}^{m} \frac{(\text{n-paraffins})_L + (\text{Iso-paraffins group } A)_L}{(\text{Total paraffins})_L} \quad (1)$$

or $$\text{Paraffin Index} = \sum_{L=n}^{m} \frac{N_L + (IP_A)_L}{[N_L + (IP_A)_L + (IP_B)_L + (IP_C)_L]}$$

In the above equation, n is a lower carbon number in the range 16 to 50, m is the upper carbon number in the range 16 to 50, $N_L$ is the amount of n-paraffin in wt. % for each individual carbon number L, and $(IP)_L$ is the amount of iso-paraffins in wt. % for each individual carbon number L. The subscripts A, B and C represent the different groups of iso-paraffins from the Table 1 above.

The process of gathering data shown in FIG. 1 and Table 1 above is repeated for a set of standard non-formulated samples. For purposes of calculating the Paraffin Index, the sample may be formulated or non-formulated since the Paraffin Index is independent of the adpak used to formulate the sample. On the other hand, the MRV for each sample is measured on a formulated sample since the MRV is influenced by the adpak used to formulate the sample, and the Paraffin Index is calculated based on the 2D GC analysis. The same adpak is used to formulate each sample. The results are plotted in a graph with measured MRV of formulated baseoil being the Y-axis and Paraffin Index being the X-axis. This will produce a graph containing the scatter data for the standard sample set. A linear line fit is applied through the data points using conventional least squares techniques. This regression technique is demonstrated in FIG. 3 for a set of data points (see Example 5). The MRV for other new formulated baseoil samples can be further predicted from the linear correlation equation:

MRV=(a)(Paraffin Index)−(b)

where (a) is the slope and (b) is the intercept.

The traditional MRV measurement requires large amount of a finished lubricating oil, such as but not limited to, an engine oil sample (150 to 200 ml) and also needs long test periods (>45 hrs) at low temperature between −10° C. and −40° C. In many instances, the viscometric properties of baseoil cannot translate into the low temperature flow property of formulated engine oil. It is highly desirable to develop an analytic tool that can precisely predict a basestock's formulated PCMO low temperature performance in a rapid test. The precise MRV prediction using advance 2D GC technique can dramatically reduce the time and cost related to the conventional MRV test.

The current analytical method can be applied to a set of standard baseoils by measuring paraffin and iso-paraffin group concentrations. The paraffin index of the standard baseoils will be calculated based on equation stated above. The user first has to establish a correlation between measured MRV of formulated baseoil and paraffin index for the standard baseoil. The MRV of the interested baseoils can be further predicted based on the correlation of MRV and paraffin index using 2D GC measurement.

This invention may be further understood by reference to the following non-limiting examples.

EXAMPLES

Example 1

Feed Composition

A commercial solvent dewaxed basestock was used as the feed in all trim dewaxing experiments. The basestock is a mixture containing approximately 81 wt. %, based on basestock, of light basestock and approximately 19 wt. % medium basestock. The basestock properties are summarized in Table 2.

TABLE 2

| Solvent Dewaxed Basestock Properties | |
|---|---|
| Density, g/cc | 0.844 |
| Boiling Range 2% to 98% off, ° F. | 690-910 |
| Kinematic Viscosity at 40° C., cSt | 23.3 |
| Kinematic Viscosity at 100° C., cSt | 4.6 |
| Viscosity Index | 114 |
| Pour Point (ISL), ° C. | −18 |
| UV Total Aromatics, mmol/kg | 18.5 |
| Saybolt Color | >+30 |
| GCD Noack Volatility, wt % | 15.2 |
| Sulfur, wppm | <10 |
| Nitrogen, wppm | <1 |
| CCS (formulated 5W30 engine oil), cp | 5790 |
| MRV (formulated 5W30 engine oil), cp | 36211 |

Example 2

Hydrodewaxing Catalysts

The catalysts employed in the trim hydrodewaxing process are described as follows. Catalyst A is 65 wt. % ZSM-48 on 35 wt. % alumina loaded with Pt. Catalyst B is a Pt loaded silicoaluminophosphate designated as ECR-42 on alumina (65/35 wt. %) and described in U.S. Pat. No. 6,303,534. Catalyst C is amorphous silica/alumina loaded with Pt. Catalyst D is 65/35 H-ZSM-48/alumina and is not metal loaded. Catalyst E is self-bound H-ZSM-5. The general catalyst properties and pre-treatment are described in Table 3.

TABLE 3

Trim Hydrodewaxing Catalyst Properties

| Catalsyt Name | Catalyst A | Catalyst B | Catalyst C | Catalyst D | Catalyst E |
|---|---|---|---|---|---|
| Pt loading (%) | 0.62 | 0.6 | 0.78 | 0 | 0 |
| H/Pt | 1.16 | 1.16 | 0.65 | N/A | N/A |
| Support | ZSM-48 | ECR-42 | $SiO_2/Al_2O_3$ | H-ZSM-48 | H-ZSM-5 |
| Binder | $Al_2O_3$ | $Al_2O_3$ | N/A | $Al_2O_3$ | N/A |
| Surface Area | 247 | 287 | 287 | 239 | N/A |
| Alpha | 24 | 39 | N/A | 20 | 47 |
| Catalyst Volume | 10 | 10 | 10 | 5 | 5 |
| Pre-sulfidation | Yes | No | No | No | No |

Example 3

Production of Trim Dewaxed Baseoils

The trim dewaxing studies were performed using a continuous catalyst testing unit (CL500 unit), which consists of a liquid feed system with a syringe pump, a fixed-bed tubular reactor with a three-zone furnace, liquid product collection, and an on-line HP Micro Refinery Analyzer (MTI) GC for gas analysis. Typically, 5-10 cc of catalyst was sized to 14/20 mesh and charged in an up-flow ⅜-inch (9.525-mm) stainless steel reactor containing a ⅛-inch (3.175-mm) thermowell. After the unit was pressure tested, the catalyst was dried at 300° C. for 2 hours with 250 cc/minute $N_2$ at ambient pressure. If pre-sulfidation of the catalyst was required, 2% $H_2S$ in hydrogen was flowed through the catalyst bed at 100 sccm (standard cc/minute) for 1 hour. Upon completion of the catalyst treatment, the reactor was cooled to 150° C., the unit pressure was set to 1000 psig (6996 kPa) by adjusting the Mity-Mite back-pressure regulator and the gas flow was switched from $N_2$ to $H_2$. Liquid feedstock was introduced into the reactor at the desired liquid hourly space velocity (LHSV). Once the liquid feed reached the downstream knockout pot, the reactor temperature was increased to the target value. A material balance (MB) was initiated until the unit was lined out for 6 hours. The total liquid product (TLP) was collected in the MB dropout pot. Gas samples were analyzed with an on-line Hewlett Packard MTI refinery gas chromatograph (GC) equipped with both thermal conductivity detector (TCD) and flame ionization detector (FID). A series of runs were performed to understand the catalyst activity/product properties as function of the process variables, such as liquid hourly space velocity (LHSV) and process temperature. The TLP product from each balance was cut at 370° C. by batch distillation. The properties of the 370° C.+ dewaxed oil were analyzed.

The feed and basestock produced as described above were then blended to make a 5W-30 passenger car motor oil (PCMO). The above basestock was a lighter viscosity than required for the finished 5W-30 oil and hence a second basestock which was somewhat heavier was added to all the blends to hit a base oil desired viscosity target. A commercial additive package for GF-3 engine oils was then added to make the formulated oil. This package consists of a detergent/inhibitor package, a viscosity modifier, and a pour point depressant. The package utilized and the second basestock were constants in all the blends, only the light basestock was varied. The formulated oils were tested for cold flow property with a mini rotary viscometer (MRV), according to the ASTM D4684 method.

Example 4

2D GC Measurement of Baseoil Composition and Paraffin Index Analysis

The 2D GC (GC×GC) system consists of an Agilent 6890 gas chromatograph (Agilent Technology, Wilmington, Del.) configured with inlet, columns, and detectors. A split/splitless inlet system with an eight-vial tray autosampler was used. The two-dimensional capillary column system utilizes a non-polar first column (BPX-5, 30 meter, 0.25 mm I.D., 1.0 μm film), and a polar (BPX-50, 9 meter, 0.25 mm I.D., 0.25 μm film), second column. Both capillary columns are the products of SGE Inc. Austin, Tex. BPX-50 is a column containing 50% Phenyl Polysilphenylene-siloxane. A dual jet thermal modulation assembly based on Zoex technology (Zoex Corp. Lincoln, Nebr.) which is liquid nitrogen cooled "trap-release" dual jet thermal modulator is installed between these two columns. A flame ionization detector (FID) is used for the signal detection. A 0.2 microliter sample was injected with 75:1 split at 300° C. from Inlet. Carrier gas is programmed from 1.5 ml/minute with 0 minute hold and 0.05 ml/minute per minute increment to 5.0 ml/minute with 0 minute hold. The oven was programmed from 210° C. with 0 minute hold and 1.5° C. per minute increment to 315° C. with 0 minute hold. The total GC run time was 70 minutes. The modulation period was 10 seconds. The sampling rate for the detector was 100 Hz. After data acquisition, it was processed for qualitative and quantitative analysis. The qualitative analysis converted data to a two-dimensional image that was processed by a commercial program, "Transform" (Research Systems Inc., Boulder, Colo.). The two-dimensional image was further processed by "PhotoShop" program (Adobe System Inc., San Jose, Calif.) to generate publication-ready images. An in-house program was used to quantify the peak volumes.

Figure 2:
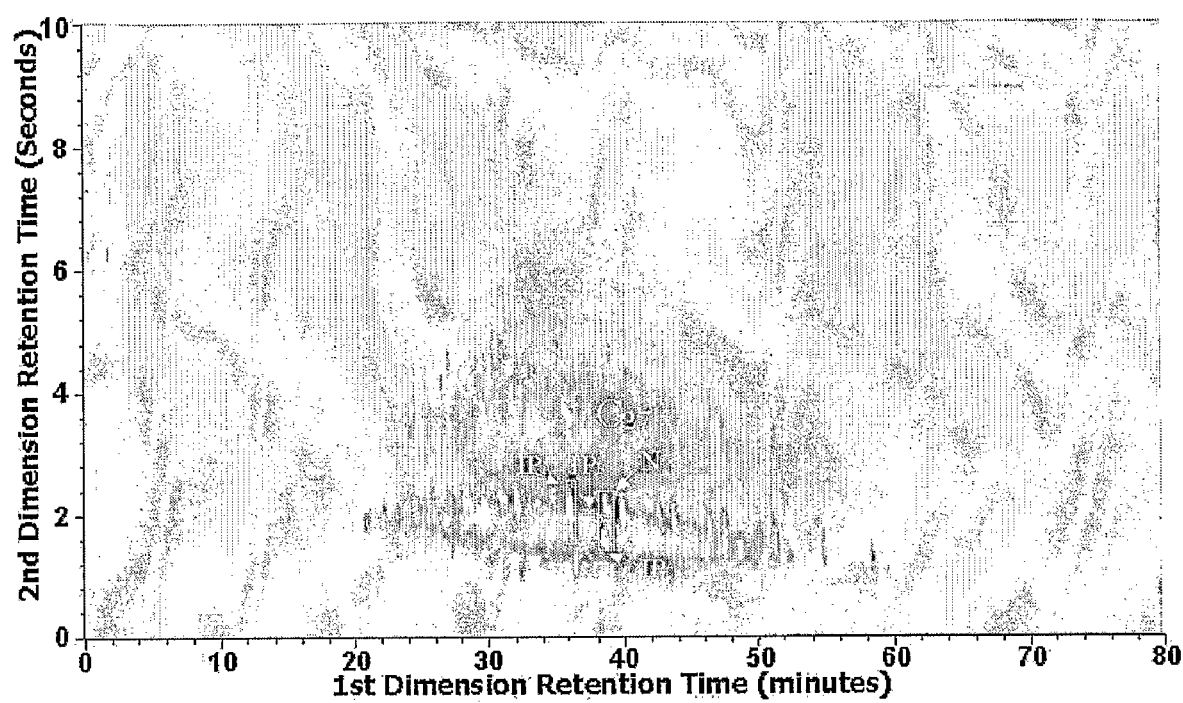
FIG. 2 is a 2D GC (GC×GC) chromatogram of the feedstock of Example 1.

FIG. 2 presents a 2D GC (GC×GC) chromatogram of the feedstock of Example 1. Using $C_{27}$ as an example, the chromatogram demonstrates the detailed n-paraffins (N) and iso-paraffins (IP) identifications and selected integration volumes of identified components. Since all iso-paraffins are not completely resolved in the two-dimensional space, the iso-paraffins have been grouped into three regions, $IP_A$, $IP_B$, and $IP_C$, at each associated carbon number of the baseoil components. While integrating the identified peaks through the entire retention time of the 2D GC chromatogram (in the range of $C_{23}$ to $C_{31}$), the weight percentage of n-paraffin and iso-paraffins at each associated carbon number can be quantitatively obtained. Table 4 shows a typical weight percentage of n-paraffins and iso-paraffins at each associated carbon numbers in the feedstock described in Example 1.

TABLE 4

Feedstock Composition Based on 2D-GC Chromatogram

| | Carbon Number | | | | | | | | |
|---|---|---|---|---|---|---|---|---|---|
| | 23 | 24 | 25 | 26 | 27 | 28 | 29 | 30 | 31 |
| N | 0.27 | 0.66 | 0.95 | 0.84 | 1.00 | 0.79 | 0.51 | 0.41 | 0.28 |
| $IP_A$ | 0.14 | 0.66 | 1.34 | 1.76 | 1.88 | 1.62 | 1.30 | 1.04 | 0.68 |
| $IP_B$ | 0.42 | 0.89 | 1.46 | 1.52 | 1.71 | 1.52 | 1.16 | 0.79 | 0.54 |
| $IP_C$ | 0.09 | 0.26 | 0.65 | 1.02 | 0.62 | 0.58 | 0.42 | 0.32 | 0.22 |

The Paraffin Index for this specific sample is calculated over a given carbon range bounded by a lower carbon number, n, and an upper carbon number, m, by summing at each carbon number (L) the ratio of (n-paraffins plus the A group of isoparaffins) to the (n-paraffins plus the A, B and C group of isoparaffins). The mathematical expression of Paraffin Index is described as follows:

$$\text{Paraffin Index} = \sum_{L=n}^{m} \frac{(n\text{-}paraffin)_L + (\text{Iso-paraffins group }A)_L}{(\text{Total paraffins})_L}$$

or $$\text{Paraffin Index} = \sum_{L=n}^{m} \frac{N_L + (IP_A)_L}{[N_L + (IP_A)_L + (IP_B)_L + (IP_C)_L]}$$

where n and m represent lower and upper carbon numbers of lube baseoil components in the carbon number range from 16 to 50. $N_L$ is the amount of n-paraffin in wt. % for each individual carbon number L, $(IP_A)_L+(IP_B)_L+(IP_C)_L$ represents the whole of all the isoparaffins with retention times between two consecutive carbon numbers of n-paraffins (such as between $nC_{26}$ and $nC_{27}$). A sample calculation for the Paraffin Index based on Table 4 is as follows for the carbon number range from 23 to 31.

For $C_{23}$: carbon number L=23, N=0.27, $IP_A$=0.14, $IP_B$=0.42, $IP_C$=0.09:

$$\text{Ratio value of } C_{23} = \frac{N_{23} + (IP_A)_{23}}{[N_{23} + (IP_A)_{23} + (IP_B)_{23} + (IP_C)_{23}]}$$

$$= \frac{0.27 + 0.14}{(0.27 + 0.14 + 0.42 + 0.09)}$$

$$= 0.44$$

For $C_{24}$: carbon number L=24, N=0.66, $IP_A$=0.66, $IP_B$=0.89, $IP_C$=0.26:

$$\text{Ratio value of } C_{24} = \frac{N_{24} + (IP_A)_{24}}{[N_{24} + (IP_A)_{24} + (IP_B)_{24} + (IP_C)_{24}]}$$

$$= \frac{0.66 + 0.66}{(0.66 + 0.66 + 0.89 + 0.26)}$$

$$= 0.53$$

Similarly, the ratio value of $C_{25}$ to $C_{31}$ are 0.52, 0.51, 0.55, 0.53, 0.57, 0.56, respectively. The sum of ratio value of $C_{23}$ to $C_{31}$ is 0.44+0.53+0.52+0.51+0.55+0.53+0.53+0.57+0.56=4.74, which is the value of the Paraffin Index of baseoil feed sample. This corresponds to the first value in Table 5 below.

Example 5

Correlation of Paraffin Index to Formulated Engine Oil MRV

For each trim HDW lube baseoil sample, based on the 2D GC analysis, the paraffin content can be quantitatively obtained and Paraffin Index can be calculated from the equation defined in the previous example. Table 5 summarizes the Paraffin Index and the measured MRV for the trim dewaxed baseoil samples studied.

TABLE 5

| Trim HDW Catalyst | Reaction Temperature (° C.) | Pour Point (° C.) | Paraffin Index | Measured Formulated Oil MRV (cP) |
|---|---|---|---|---|
| Feed | | −18 | 4.74 | 36211 |
| Catalyst D | 270 | −19 | 4.73 | 33700 |
| Catalyst E | 255 | −20 | 4.61 | 31400 |
| Catalyst B | 260 | −17 | 4.63 | 30874 |
| Catalyst D | 290 | −19 | 4.68 | 29600 |
| Catalyst C | 320 | −19 | 4.68 | 27876 |
| Catalyst C | 325 | −18 | 4.64 | 26870 |
| Catalyst C | 330 | −21 | 4.66 | 26050 |
| Catalyst E | 260 | −22 | 4.52 | 25800 |
| Catalyst B | 270 | −19 | 4.56 | 25306 |
| Catalyst C | 340 | −19 | 4.56 | 23170 |
| Catalyst E | 265 | −22 | 4.47 | 23000 |
| Catalyst A | 290 | −19 | 4.38 | 19536 |
| Catalyst D | 330 | −22 | 4.45 | 19100 |
| Catalyst D | 340 | −24 | 4.40 | 17300 |
| Catalyst D | 340 | −25 | 4.40 | 17300 |
| Catalyst A | 295 | −21 | 4.34 | 17004 |
| Catalyst B | 280 | −21 | 4.37 | 16130 |
| Catalyst E | 275 | −26 | 4.37 | 16100 |
| Catalyst E | 280 | −32 | 4.38 | 14800 |
| Catalyst B | 290 | −29 | 4.32 | 12700 |
| Catalyst A | 300 | −27 | 4.30 | 12675 |
| Catalyst A | 300 | −30 | 4.29 | 12675 |

Figure 3:
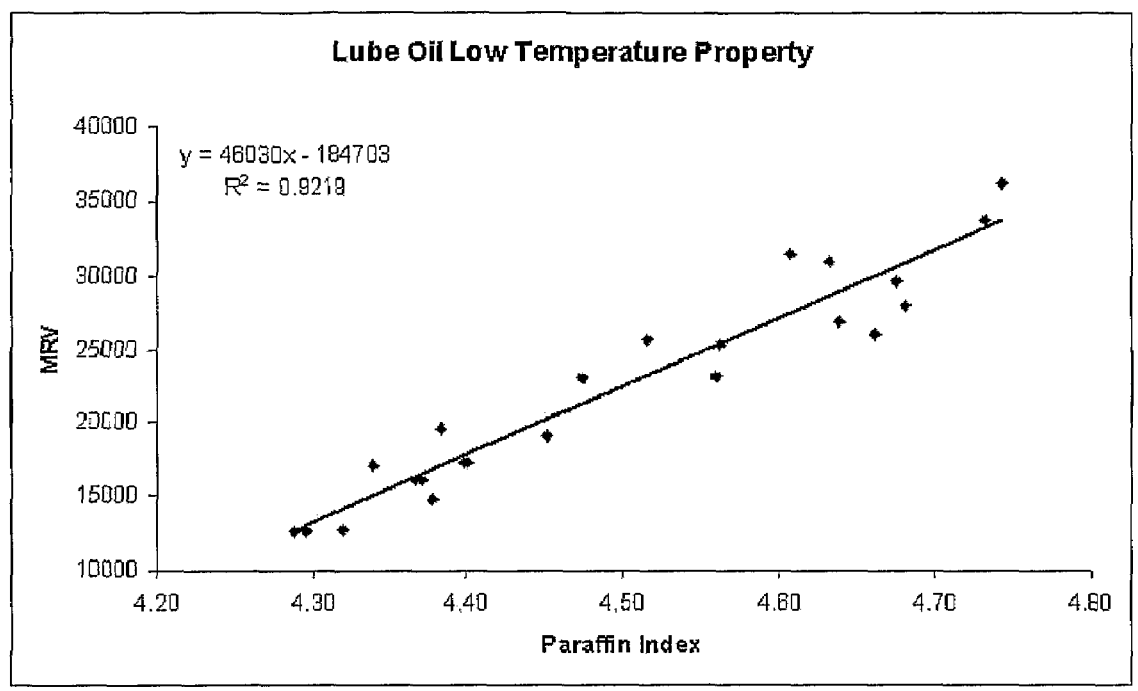
FIG. 3 illustrates the correlation plot between the Paraffin Index and measured formulated baseoil MRV for trim dewaxed baseoil.

The results from Table 5 are plotted in a graph with measured MRV being the Y-axis and Paraffin Index being the X-axis. This produces a graph containing the scatter data for the studied samples. A linear line fit is applied through the data points using conventional least squares techniques. The linear regression line is demonstrated in FIG. 3 for a set of data points of the studied trim HDW samples. FIG. 3 illustrates the correlation plot between the Paraffin Index and MRV for formulated trim dewaxed baseoil studied using various catalysts and process conditions.

The correlation was established based on the least-square fit of measured MRV and calculated Paraffin index listed in Table 5. We use the excel linear line fit function which can automatically calculate the linear equation listed in FIG. 3. The linear correlation between MRV of the formulated trim dewaxed baseoils and Paraffin Index of the trim dewaxed baseoils is expressed as:

MRV=46030×Paraffin Index−184703     (2)

where slope of the linear equation is 46030 and intercept is −184703. The established linear correlation showed the coefficient of variation, $R^2$, equal to 0.9219.

Utilizing the equation 2 stated above, a predicted formulated engine oil MRV value can be calculated based on the Paraffin Index of trim dewaxed baseoil samples. For example, the baseoil produced at 270° C. using catalyst D was analyzed by 2D GC and the Paraffin Index of this baseoil sample was calculated as 4.73 based on the 2D GC data analysis. We can substitute the obtained paraffin index (4.73) into Equation 2. The predict formulated engine oil MRV of the sample is calculated as following:

Predicted Formulated Engine Oil MRV=46030×4.73−184703=33141

Table 6 lists measured MRV, predicted MRV and the percentage of the difference for trim dewaxed baseoil studied using various catalysts and process conditions. We can apply the same procedure to new baseoil samples to obtain the predicted formulated engine oil MRV.

TABLE 6

The Measured, Predicted and the Variation of Formulated Engine Oil MRV of the Samples Studied

| Trim HDW Catalyst | Reaction Temperature (° C.) | Paraffin Index | MRV Measure (cP) | MRV Predicted (cP) | Difference (%) |
|---|---|---|---|---|---|
| Feed |  | 4.74 | 36211 | 33619 | 7 |
| Catalyst D | 270 | 4.73 | 33700 | 33141 | 2 |
| Catalyst E | 255 | 4.61 | 31400 | 27343 | 13 |
| Catalyst B | 260 | 4.63 | 30874 | 28531 | 8 |
| Catalyst D | 290 | 4.68 | 29600 | 30501 | 3 |
| Catalyst C | 320 | 4.68 | 27876 | 30769 | 10 |
| Catalyst C | 325 | 4.64 | 26870 | 28814 | 7 |
| Catalyst C | 330 | 4.66 | 26050 | 29898 | 15 |
| Catalyst E | 260 | 4.52 | 25600 | 23157 | 10 |
| Catalyst B | 270 | 4.56 | 25306 | 25329 | 0 |
| Catalyst C | 340 | 4.56 | 23170 | 25191 | 9 |
| Catalyst E | 265 | 4.47 | 23000 | 21261 | 8 |
| Catalyst A | 290 | 4.38 | 19536 | 17090 | 13 |
| Catalyst D | 330 | 4.45 | 19100 | 20230 | 6 |
| Catalyst D | 340 | 4.40 | 17300 | 17769 | 3 |
| Catalyst D | 340 | 4.40 | 17300 | 17858 | 3 |
| Catalyst A | 295 | 4.34 | 17004 | 15018 | 12 |
| Catalyst B | 280 | 4.37 | 16130 | 16475 | 2 |
| Catalyst E | 275 | 4.37 | 16100 | 16269 | 1 |
| Catalyst E | 280 | 4.38 | 14800 | 16824 | 14 |
| Catalyst B | 290 | 4.32 | 12700 | 14125 | 11 |
| Catalyst A | 300 | 4.30 | 12675 | 13039 | 3 |
| Catalyst A | 300 | 4.29 | 12675 | 12686 | 0 |

According to the MRV test method (ASTM D4684-02a), the statistical repeatability of MRV test is 13.2% from mean at test temperature of −35° C. In addition, the reproducibility of MRV test is 35.8% from mean at test temperature of −35° C. As seen in the Table 6, all variations between predicted and measured MRV are below the reproducibility uncertainty range. Therefore, we can conclude that the new MRV correlation tool developed by 2D GC technique provides an acceptable accuracy for prediction of MRV of the formulated trim dewaxed baseoils.

The invention claimed is:

1. A process for predicting the Mini Rotary Viscometer (MRV) properties of formulated oils which comprises:
   (a) injecting a basestock sample into a first column of a 2-dimensional gas chromatograph, said first column being coated with a non-polar material to separate the basestock sample into a series of first dimension sample components having a first set of retention times;
   (b) injecting the separated first dimension sample components from step (a) into a second column coated with a semi-polar material to further separate the separated first dimension sample components into second dimension sample components having a second set of retention times;
   (c) subjecting the first and second sets of retention times to qualitative analysis to identify n-paraffin and iso-paraffin components or groupings thereof and to quantitative analysis to identify the quantity of the n-paraffin components and iso-paraffin components or groupings thereof having carbon numbers in the lubricant basestock range;
   (d) grouping the iso-paraffin components into x groupings where x is a number from 0 to 3 for each identified individual lube paraffin in the carbon number range from 16 to 50;
   (e) selecting a lower carbon number n and an upper carbon number m;
   (f) identifying the n-paraffin and a first, second and third iso-paraffin group A, B and C for each individual carbon number over the range from n to m;
   (g) calculating a Paraffin Index over a given carbon range bounded by a lower carbon number, n, and an upper carbon number m, wherein the Paraffin Index is calculated by:

$$\text{Paraffin Index} = \sum_{L=n}^{m} \frac{(\text{n-paraffin})_L + (\text{Iso-paraffins group } A)_L}{(\text{Total paraffins})_L}$$

where L is the carbon number of the identified paraffins over the carbon range from n to m in the baseoil sample, (n-paraffin)L is the amount of the normal paraffin at each individual carbon number, (Iso-paraffins group A)L is the amount of iso-paraffins in a first group A at each individual carbon number, and (Total paraffins)L is the sum of n-paraffin plus iso-paraffin groups A, B and C at each individual carbon number;
   (h) repeating steps (a)-(g) for a series of basestock samples;
   (i) measuring the MRV for a series of formulated basestock samples;
   (j) plotting measured MRV of the formulated basestock samples versus Paraffin Index of basestock samples to produce a plot having a slope (M) and a y-intercept (B); and
   (k) calculating the predicted MRV using the equation: Predicted MRV=(M)* (Paraffin Index)+(B).

2. The process of claim 1 wherein the basestock has been solvent extracted, hydrotreated or extracted and hydrotreated.

3. The process of claim 1 wherein the basestock has been dewaxed.

4. The process of claim 3 wherein dewaxing is by at least one of solvent dewaxing or catalytic dewaxing.

5. The process of claim 4 wherein catalytic dewaxing is under effective dewaxing conditions.

6. The process of claim 5 wherein effective dewaxing conditions include temperatures between about 200° C. to about 400° C., pressures between about 2860 to about 20786 kPa, hydrogen treat gas rates of about 89 to about 890 m$^3$/m$^3$, and liquid hourly space velocities of about 0.1 to about 10 V/V/hr.

7. The process of claim 1 wherein the formulated basestock samples have been formulated with an additive package.

8. The process of claim 1 wherein the non-polar material has a polarity between 0 and 20.

9. The process of claim 1 wherein the semi-polar material has a polarity between 20 and 50.

10. The process of claim 1 wherein separated first dimension sample components are sent to a modulator.

11. The process of claim 8 wherein the non-polar material is a methyl silicon polymer.

12. The process of claim 9 wherein the semi-polar material is a methyl silicon polymer in which at least some of the methyl groups have been substituted by phenyl.

13. The process of claim 1 wherein the retention times for separated sample components from the second dimension are coupled with the retention times for sample components from the first dimension sample components to form a comprehensive two-dimensional chromatogram.

14. The process of claim 1 wherein the iso-paraffin components are grouped into 3 groups.

15. The process of claim 14 wherein the total paraffins are the sum of the n-paraffin plus the 3 groups of iso-paraffins.

16. The process of claim 1 wherein n-paraffin is the amount of normal paraffin for any given carbon number L.

17. The process of claim 1 wherein the basestock sample is non-formulated.

18. The process of claim 1 wherein the formulated basestock samples are formulated with an additive package.

19. The process of claim 18 wherein the additive packages contains at least one component selected from dispersants, detergents, wear inhibitors, antioxidants, rust inhibitors, demulsifiers, extreme pressure agents, friction modifiers, multifunction additives, viscosity index improvers, pour point depressants, and foam inhibitors, solvents.

20. The process of claim 1 wherein the formulated oils are for use in passenger car internal combustion engines.

21. The process of claim 1 wherein x is 3.

* * * * *